United States Patent
Suzuki

(10) Patent No.: US 10,285,913 B2
(45) Date of Patent: May 14, 2019

(54) DENTAL POLYMERIZABLE COMPOSITION, DENTAL TEMPORARY CEMENT, DENTAL FILLING MATERIAL, DENTURE LINER, AND DENTAL TISSUE CONDITIONER

(71) Applicant: KURARAY NORITAKE DENTAL INC., Kurashiki-shi (JP)

(72) Inventor: Kenji Suzuki, Tainai (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 14 days.

(21) Appl. No.: 15/121,188

(22) PCT Filed: Feb. 10, 2015

(86) PCT No.: PCT/JP2015/000616
§ 371 (c)(1),
(2) Date: Aug. 24, 2016

(87) PCT Pub. No.: WO2015/129180
PCT Pub. Date: Sep. 3, 2015

(65) Prior Publication Data
US 2017/0014312 A1    Jan. 19, 2017

(30) Foreign Application Priority Data
Feb. 25, 2014    (JP) .................... 2014-034414

(51) Int. Cl.
C08F 2/46 (2006.01)
C08F 2/50 (2006.01)
C08G 61/04 (2006.01)
A61K 6/083 (2006.01)
A61K 6/00 (2006.01)
C08F 265/06 (2006.01)

(52) U.S. Cl.
CPC ............ A61K 6/0835 (2013.01); A61K 6/005 (2013.01); A61K 6/0023 (2013.01); A61K 6/0026 (2013.01); A61K 6/0052 (2013.01); C08F 265/06 (2013.01)

(58) Field of Classification Search
CPC .... A61K 6/0835; A61K 6/005; A61K 6/0026; A61K 6/0052; C08F 265/06
USPC ............... 522/48, 47, 6, 189, 184, 1; 520/1
See application file for complete search history.

(56) References Cited

U.S. PATENT DOCUMENTS

| | | | |
|---|---|---|---|
| 5,075,107 A * | 12/1991 | Katakura | ............... A61K 6/083 106/35 |
| 5,866,632 A | 2/1999 | Hashimoto et al. | |
| 6,037,388 A | 3/2000 | Hashimoto et al. | |
| 7,906,565 B2 | 3/2011 | Hashiguchi et al. | |
| 2008/0293011 A1* | 11/2008 | Hashiguchi | .......... A61K 6/0026 433/168.1 |
| 2012/0196952 A1* | 8/2012 | Suzuki | ................. A61K 6/0023 523/116 |
| 2015/0051603 A1 | 2/2015 | Chisholm et al. | |

FOREIGN PATENT DOCUMENTS

| | | |
|---|---|---|
| JP | 60-8214 A | 1/1985 |
| JP | 7-101616 A | 4/1995 |
| JP | 2000-159621 A | 6/2000 |
| JP | 2006-136649 A | 6/2006 |
| JP | 2006-225281 A | 8/2006 |
| JP | 2009-254808 A | 11/2009 |
| JP | 2010-208964 A | 9/2010 |
| JP | 2013-203718 A | 10/2013 |
| WO | 2011/048802 A1 | 4/2011 |
| WO | WO 2013/144590 A1 | 10/2013 |

OTHER PUBLICATIONS

International Search Report dated May 19, 2015 in PCT/JP2015/000616 Filed Feb. 10, 2015.
Extended European Search Report dated Oct. 12, 2017 in Patent Application No. 15754548.4.

* cited by examiner

Primary Examiner — Jessica Whiteley
(74) Attorney, Agent, or Firm — Oblon, McClelland, Maier & Neustadt, L.L.P.

(57) ABSTRACT

A dental polymerizable composition according to the present invention includes a (meth)acrylic acid ester polymer (a), a polymerizable monomer (b) including a (meth)acrylic acid ester and/or a (meth)acrylamide, and a polymerization initiator (c). The (meth)acrylic acid ester polymer (a) includes a (meth)acrylic acid ester homopolymer having a glass transition temperature of 25° C. to 50° C. and/or a random copolymer of a (meth)acrylic acid ester whose homopolymer has a glass transition temperature higher than 37° C. and a (meth)acrylic acid ester whose homopolymer has a glass transition temperature lower than 37° C. The (meth)acrylic acid ester polymer (a) has a glass transition temperature of 25° C. to 50° C., has tan δ at 37° C. of 0.10 or more as determined by dynamic mechanical analysis, and has no melting point.

8 Claims, No Drawings

DENTAL POLYMERIZABLE COMPOSITION, DENTAL TEMPORARY CEMENT, DENTAL FILLING MATERIAL, DENTURE LINER, AND DENTAL TISSUE CONDITIONER

TECHNICAL FIELD

The present invention relates to a dental polymerizable composition and to a dental temporary cement, a dental filling material, a denture liner, and a dental tissue conditioner that include the dental polymerizable composition.

BACKGROUND ART

Various dental materials are used for restorative treatment of teeth and examples thereof include inorganic materials and organic materials. Among the organic materials, polymerizable compositions containing a (meth)acrylic acid ester, a polymerization initiator, and a filler are widely used. The polymerizable compositions for restorative treatment of teeth can be broadly classified into two groups depending on their hardness obtained after curing. One of the groups consists of soft materials which are flexible when cured, and the soft materials are used, for example, in liners for denture bases, adhesive materials for oral cavity tissues such as temporary sealing materials, and shock-absorbing materials. The recent development of dentistry has created a need for a new soft material.

For example, it is common practice to attach a denture to a patient who has lost teeth for a cause such as aging. When a denture is used, a denture liner or a tissue conditioner is used in combination to improve the usability, such as to enable holding of the denture for a long time or reduce the shock to the jaw. Such a denture liner or tissue conditioner needs to have appropriate flexibility and shock-absorbing capacity.

Implantation has also become widely used for treatment of patients who have lost teeth for a cause such as aging. An implant is composed of an artificial tooth root to be embedded directly in the jawbone, a tooth crown placed above the artificial tooth root, and a tooth base, called an abutment, for connecting the artificial tooth root to the tooth crown. These parts are bonded together when used. This bonding is done with a temporary cement in some cases. The bonding portion needs to be removable since the implant must occasionally be retrieved for a maintenance process such as washing. A requirement for the temporary cement is therefore that its cured product should have appropriate flexibility. In the meantime, a tooth root of a living body includes a tissue called a periodontal membrane, and this tissue absorbs a biting-induced shock to reduce the transmission of the shock to the jawbone. However, a site treated with an implant lacks this periodontal membrane, and as such could permit shock transmission to the jawbone, which is why the artificial tooth root is required to reduce the biting-induced shock.

Addition of a flexible polymer is known as a method for imparting flexibility or shock-absorbing capacity to a cured product of a dental polymerizable composition. For example, Patent Literature 1 describes a polymerizable composition suitable for use in a temporary cement or a mobile tooth fixing material, the polymerizable composition containing an acrylic block copolymer added to improve the flexibility of a cured product of the composition. Patent Literature 2 describes a dental tissue conditioner to which is added an acrylic polymer powder having a glass transition temperature within a predetermined range. This dental tissue conditioner has the property of maintaining its original flexibility. Patent Literature 3 describes a dental adhesive containing a copolymer of a long-chain alkyl (meth)acrylate and a short-chain alkyl (meth)acrylate, the copolymer having a glass transition temperature within a predetermined range and a melting point within a predetermined range. This dental adhesive has good removability and adhesiveness. Patent Literature 4 describes a dental implant-protecting material in which a soft material is used, the protecting material having a loss tangent at 37° C. within a predetermined range. This dental implant-protecting material serves to dampen a biting-induced load on a fixture of an implant. That is, this dental implant-protecting material has good shock-reducing capacity. Patent Literature 5 describes a dental temporary cement composition containing a particular type of styrene block copolymer. This dental temporary cement has good adhesiveness suitable for temporary cementation to a metal or a ceramic.

CITATION LIST

Patent Literature

Patent Literature 1: WO 2011/048802 A1
Patent Literature 2: JP 2006-225281 A
Patent Literature 3: JP 2006-136649 A
Patent Literature 4: JP 2009-254808 A
Patent Literature 5: JP 2013-203718 A

SUMMARY OF INVENTION

Technical Problem

The polymerizable composition of Patent Literature 1 includes an acrylic block copolymer having a polymer block acting as a hard segment, which fact limits the effect of making flexible a cured product of the polymerizable composition. Patent Literature 1 makes no statement on the shock-absorbing capacity of a cured product of the polymerizable composition.

Non-polymerizable materials, such as the dental tissue conditioner described in Patent Literature 2 and the dental adhesive described in Patent Literature 3, are generally susceptible to penetration of coloring matters and may have poor stain resistance.

The dental implant-protecting material described in Patent Literature 4 contains a liquid polymer having a molecular weight of 10000 or less and an oligomer component having a molecular weight of 500 or less. Given this fact, the dental implant-protecting material possibly has a problem in that its shape retention tends to be poor or its transparency is easily reduced by water penetration.

As for the dental temporary cement composition described in Patent Literature 5, it may be difficult to dissolve the styrene block copolymer in a (meth)acrylic acid ester due to the difference in polarity between the styrene block copolymer and the (meth)acrylic acid ester. This is why, for the dental temporary cement composition described in Patent Literature 5, the (meth)acrylic acid ester that can be used to dissolve the styrene block copolymer is limited to particular (meth)acrylic acid esters.

It is therefore an object of the present invention to provide a polymerizable composition that shows good flexibility and shock-absorbing capacity when cured and that is suitable for use in dental temporary cements, dental filling materials, denture liners, and dental tissue conditioners. Another object of the present invention is to provide a dental temporary cement, a dental filling material, a denture liner, and a dental tissue conditioner that include the dental polymerizable composition.

Solution to Problem

The present invention provides a dental polymerizable composition including: a (meth)acrylic acid ester polymer (a) including a (meth)acrylic acid ester homopolymer having a glass transition temperature of 25° C. to 50° C. and/or a random copolymer of a (meth)acrylic acid ester whose homopolymer has a glass transition temperature higher than 37° C. and a (meth)acrylic acid ester whose homopolymer has a glass transition temperature lower than 37° C., the (meth)acrylic acid ester polymer (a) having a glass transition temperature of 25° C. to 50° C., having tan δ at 37° C. of 0.10 or more as determined by dynamic mechanical analysis, and having no melting point; a polymerizable monomer (b) including a (meth)acrylic acid ester and/or a (meth) acrylamide; and a polymerization initiator (c).

It is preferable for the (meth)acrylic acid ester polymer (a) to be dissolved in the polymerizable monomer (b).

It is desirable for the dental polymerizable composition to further include a polymerization accelerator (d).

The present invention further provides a dental temporary cement including the above dental polymerizable composition.

The present invention further provides a dental filling material including the above dental polymerizable composition.

The present invention further provides a denture liner including the above dental polymerizable composition.

The present invention further provides a dental tissue conditioner including the above dental polymerizable composition.

Advantageous Effects of Invention

The dental polymerizable composition of the present invention shows good flexibility and shock-absorbing capacity when cured. This is why the dental polymerizable composition of the present invention is particularly suitable for use in denture liners and dental tissue conditioners, and can be suitably used also in dental temporary cements and dental filling materials.

DESCRIPTION OF EMBODIMENTS

A dental polymerizable composition of the present invention includes a (meth)acrylic acid ester polymer (a), a polymerizable monomer (b), and a polymerization initiator (c). The (meth)acrylic acid ester polymer (a) includes a (meth)acrylic acid ester homopolymer having a glass transition temperature of 250° C. to 50° C. and/or a random copolymer of a (meth)acrylic acid ester whose homopolymer has a glass transition temperature higher than 37° C. and a (meth)acrylic acid ester whose homopolymer has a glass transition temperature lower than 37° C. The (meth)acrylic acid ester polymer (a) has a glass transition temperature of 25° C. to 50° C. For the (meth)acrylic acid ester polymer (a), tan δ at 37° C. as determined by dynamic mechanical analysis is 0.10 or more. Furthermore, the (meth)acrylic acid ester polymer (a) has no melting point. That is, the (meth) acrylic acid ester polymer (a) belongs to amorphous polymers. The polymerizable monomer (b) includes a (meth) acrylic acid ester and/or a (meth)acrylamide.

(Meth)Acrylic Acid Ester Polymer (a)

The (meth)acrylic acid ester polymer (a) is used in the dental polymerizable composition of the present invention to impart flexibility and shock-absorbing capacity to a cured product of the dental polymerizable composition. The closer the glass transition temperature (Tg) of the (meth)acrylic acid ester polymer (a) is to 37° C., the better are the flexibility and shock-absorbing capacity of a cured product of the dental polymerizable composition of the present invention. Thus, Tg of the (meth)acrylic acid ester polymer (a) is preferably 30° C. to 45° C. and more preferably 35° C. to 40° C.

The greater is the tan δ at 37° C. of the (meth)acrylic acid ester polymer (a) as determined by dynamic mechanical analysis, the better is the shock-absorbing capacity of a cured product of the polymerizable composition of the present invention. The tan δ at 37° C. of the (meth)acrylic acid ester polymer (a) is 0.10 or more, preferably 0.20 or more, and more preferably 0.30 or more. The upper limit of the tan δ at 37° C. of the (meth)acrylic acid ester polymer (a) is, for example, but not limited to, 1.0.

The (meth)acrylic acid ester for forming the (meth)acrylic acid ester polymer (a) may be a (meth)acrylic acid ester whose homopolymer has a Tg of 25° C. to 50° C. or may be a mixture of a (meth)acrylic acid ester whose homopolymer has a Tg higher than 37° C. and a (meth)acrylic acid ester whose homopolymer has a Tg lower than 37° C.

When the (meth)acrylic acid ester for forming the (meth) acrylic acid ester polymer (a) is a (meth)acrylic acid ester whose homopolymer has a Tg of 25° C. to 50° C., the polymer (a) is in the form of a homopolymer of the (meth) acrylic acid ester whose homopolymer has a Tg of 25° C. to 50° C. The coupling form of the homopolymer may be any of a linear form, a branched form, a radial form, or a combination of two or more of these forms. In particular, a linear or branched homopolymer is preferably used in terms of the ease of producing the (meth)acrylic acid ester polymer (a).

Examples of the (meth)acrylic acid ester whose homopolymer has a Tg of 25° C. to 50° C. include n-propyl methacrylate, iso-butyl methacrylate, neopentyl methacrylate, phenethyl methacrylate, N,N-dimethylaminoethyl methacrylate, and glycidyl methacrylate. Among these, n-propyl methacrylate, iso-butyl methacrylate, and neopentyl methacrylate are preferred because the (meth)acrylic acid ester polymer (a) as obtained using any of these methacrylates has good solubility in the polymerizable monomer (b).

When the (meth)acrylic acid ester for forming the (meth) acrylic acid ester polymer (a) is a mixture of a (meth)acrylic acid ester whose homopolymer has a Tg higher than 37° C. and a (meth)acrylic acid ester whose homopolymer has a Tg lower than 37° C., the polymer (a) is in the form of a random copolymer. The coupling form of the random copolymer may be any of a linear form, a branched form, a radial form, or a combination of two or more of these forms. In particular, a linear or branched random copolymer is preferably used in terms of the ease of producing the (meth)acrylic acid ester polymer (a).

Examples of the (meth)acrylic acid ester whose homopolymer has a Tg higher than 37° C. include methyl methacrylate, ethyl methacrylate, iso-propyl methacrylate, sec-butyl methacrylate, tert-butyl (meth)acrylate, iso-butyl methacrylate, cyclohexyl methacrylate, adamantyl (meth) acrylate, isobornyl (meth)acrylate, phenyl methacrylate, benzyl methacrylate, phenoxyethyl methacrylate, 2-hydroxyethyl methacrylate, 2-hydroxypropyl methacrylate, and tetrahydrofurfuryl methacrylate. Among these, methyl methacrylate, ethyl methacrylate, iso-propyl methacrylate, sec-butyl methacrylate, tert-butyl (meth)acrylate, iso-butyl methacrylate, cyclohexyl methacrylate, 2-hydroxyethyl methacrylate, and tetrahydrofurfuryl methacrylate are preferred because the (meth)acrylic acid ester polymer (a) as obtained using any of these (meth)acrylates has good solubility in the polymerizable monomer (b).

Examples of the (meth)acrylic acid ester whose homopolymer has a Tg lower than 37° C. include n-butyl (meth)acrylate, n-hexyl (meth)acrylate, pentyl (meth)acrylate, 2-ethylhexyl (meth)acrylate, octyl (meth)acrylate, decyl (meth)acrylate, dodecyl (meth)acrylate, methoxyethyl (meth)acrylate, ethoxyethyl (meth)acrylate, butoxyethyl (meth)acrylate, N,N-dimethylaminoethyl (meth)acrylate, and sec-butyl acrylate. Among these, n-butyl (meth)acrylate, n-hexyl (meth)acrylate, pentyl (meth)acrylate, and 2-ethylhexyl (meth)acrylate are preferred because the resulting (meth)acrylic acid ester polymer (a) has good solubility in the polymerizable monomer (b) when any of these (meth)acrylates is used.

When the (meth)acrylic acid ester polymer (a) includes the above random copolymer, the random copolymer may include a unit derived from an acrylic acid ester other than those mentioned above and further include a unit derived from still another monomer to the extent that the effect of the present invention does not diminish. Examples of the other monomer include: vinyl monomers having a carboxyl group such as (meth)acrylic acid, maleic acid, and maleic anhydride; (meth)acrylamides; aromatic vinyl monomers such as styrene, α-methylstyrene, and p-methylstyrene; conjugated diene monomers such as butadiene and isoprene; olefin monomers such as ethylene and propylene; and lactone monomers such as ε-caprolactone and valerolactone.

The weight-average molecular weight (Mw) of the (meth)acrylic acid ester polymer (a) is preferably in the range of 10000 to 2000000, more preferably in the range of 20000 to 1000000, and even more preferably in the range of 30000 to 500000, in terms of the solubility in the polymerizable monomer (b) and the shock-absorbing capacity of a cured product of the polymerizable composition. The weight-average molecular weight as defined herein refers to a polystyrene-equivalent weight-average molecular weight as determined by gel permeation chromatography (GPC).

The method for producing the (meth)acrylic acid ester polymer (a) is not particularly limited as long as the method yields a polymer meeting the requirements of the present invention for the chemical structure. Any method employing commonly-known procedures can be used.

Polymerizable Monomer (b)

Examples of the (meth)acrylic acid ester and the (meth) acrylamide which may be included in the polymerizable monomer (b) include a monofunctional (meth)acrylic acid ester and (meth)acrylamide having one (meth)acryloyl group and a polyfunctional (meth)acrylic acid ester and (meth)acrylamide having two or more (meth)acryloyl groups.

Examples of the monofunctional (meth)acrylic acid ester and (meth)acrylamide include: 2-hydroxyethyl (meth)acrylate, 2-hydroxypropyl (meth)acrylate, 3-hydroxypropyl (meth)acrylate, 4-hydroxybutyl (meth)acrylate, 6-hydroxyhexyl (meth)acrylate, 10-hydroxydecyl (meth)acrylate, propylene glycol mono(meth)acrylate, glycerol mono(meth) acrylate, erythritol mono(meth)acrylate, N-methylol(meth) acrylamide, N-hydroxyethyl(meth)acrylamide, N,N-(dihydroxyethyl)(meth)acrylamide, methyl (meth)acrylate, ethyl (meth)acrylate, propyl (meth)acrylate, isopropyl (meth)acrylate, n-butyl (meth)acrylate, sec-butyl (meth) acrylate, t-butyl (meth)acrylate, isobutyl (meth)acrylate, n-hexyl (meth)acrylate, cyclohexyl (meth)acrylate, lauryl (meth)acrylate, cetyl (meth)acrylate, stearyl (meth)acrylate, isobornyl (meth)acrylate, benzyl (meth)acrylate, phenyl (meth)acrylate, tetrahydrofurfuryl (meth)acrylate, methoxyethyl (methacrylate), methoxydiethylene glycol (meth)acrylate, butoxyethyl (meth)acrylate, butoxydiethylene glycol (meth)acrylate, 2,3-dibromopropyl (meth)acrylate, 3-(meth) acryloyloxypropyltrimethoxysilane, 11-(meth)acryloyloxyundecyltrimethoxysilane, and these (meth)acrylamides. These may be used alone or in combination with one another. Among the above examples, methyl (meth)acrylate, ethyl (meth)acrylate, n-butyl (meth)acrylate, sec-butyl (meth)acrylate, t-butyl (meth)acrylate, isobutyl (meth)acrylate, n-hexyl (meth)acrylate, cyclohexyl (meth)acrylate, and isobornyl (meth)acrylate are preferred in that they have good miscibility with the (meth)acrylic acid ester polymer (a) and contribute to the good flexibility of a cured product of the dental polymerizable composition.

The dental polymerizable composition of the present invention may include a fluorine-containing (meth)acrylic acid ester as the polymerizable monomer (b) for the purpose of adjusting the resistance to staining by coloring matters. Examples of such a fluorine-containing (meth)acrylic acid ester include 2,2,2-trifluoroethyl (meth)acrylate, 2,2,3,3,3-pentafluoropropyl (meth)acrylate, 2-(perfluorobutyl)ethyl (meth)acrylate, 3-(perfluorobutyl)-2-hydroxypropyl (meth) acrylate, 2-(perfluorohexyl)ethyl (meth)acrylate, 3-perfluorohexyl-2-hydroxypropyl (meth)acrylate, 3-(perfluoro-3-methylbutyl)-2-hydroxypropyl (meth)acrylate, 1H,1H,3H-tetrafluoropropyl (meth)acrylate, 1H,1H,5H-octafluoropentyl (meth)acrylate, 1H,1H,7H-dodecafluoroheptyl (meth)acrylate, 1H-1-(trifluoromethyl) trifluoroethyl (meth)acrylate, and 1H,1H,3H-hexafluorobutyl (meth)acrylate. Among these, 2-(perfluorobutyl)ethyl (meth)acrylate, 2-(perfluorohexyl) ethyl (meth)acrylate, 1H,1H,5H-octafluoropentyl (meth) acrylate, 1H,1H,7H-dodecafluoroheptyl (meth)acrylate, 1H-1-(trifluoromethyl)trifluoroethyl (meth)acrylate, and 1H,1H,3H-hexafluorobutyl (meth)acrylate are preferably used, and 1H,1H,5H-octafluoropentyl (meth)acrylate and 1H,1H,7H-dodecafluoroheptyl (meth)acrylate are more preferably used, in terms of good stain resistance.

The content of the fluorine-containing (meth)acrylic acid ester in the polymerizable monomer (b) is not particularly limited. In terms of the stain resistance, the content is preferably 20 to 100 weight %, more preferably 30 to 100 weight %, and even more preferably 40 to 100 weight %.

The dental polymerizable composition of the present invention may also include an acid group-containing (meth) acrylic acid ester as the polymerizable monomer (b) for the purpose of adjusting the bond strength to a metal, another resin, or a tooth structure. Examples of such an acid group-containing (meth)acrylic acid ester include (meth)acrylic acid esters having at least one of acid groups such as a phosphoric acid group, a pyrophosphoric acid group, a thiophosphoric acid group, a phosphonic acid group, a sulfonic acid group, and a carboxylic acid group.

Examples of the (meth)acrylic acid ester having a phosphoric acid group include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth) acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl] hydrogen phosphate, bis[4-(meth)acryloyloxybutyl] hydrogen phosphate, bis[6-(meth) acryloyloxyhexyl] hydrogen phosphate, bis[8-(meth)acryloyloxyoctyl] hydrogen phosphate, bis[9-(meth) acryloyloxynonyl] hydrogen phosphate, bis[10-(meth) acryloyloxydecyl] hydrogen phosphate, 1,3-di(meth) acryloyloxypropyl dihydrogen phosphate, 2-(meth) acryloyloxyethylphenyl hydrogen phosphate, 2-(meth) acryloyloxyethyl-2-bromoethyl hydrogen phosphate, and bis[2-(meth)acryloyloxy-(1-hydroxymethyl)ethyl] hydrogen phosphate; and their acid chlorides, alkali metal salts, and ammonium salts. These may be used alone or in combination with one another.

Examples of the polyfunctional (meth)acrylic acid ester and (meth)acrylamide include difunctional aromatic (meth) acrylic acid esters and (meth)acrylamides, difunctional aliphatic (meth)acrylic acid esters and (meth)acrylamides, and tri- or higher-functional (meth)acrylic acid esters and (meth) acrylamides.

Examples of the difunctional aromatic (meth)acrylic acid esters and (meth)acrylamides include 2,2-bis((meth)acryloyloxyphenyl)propane, 2,2-bis[4-(3-(meth)acryloyloxy)-2-hydroxypropoxyphenyl]propane (commonly called "Bis-GMA"), 2,2-bis(4-(meth)acryloyloxyethoxyphenyl) propane, 2,2-bis(4-(meth)acryloyloxypolyethoxyphenyl) propane, 2,2-bis(4-(meth)acryloyloxydiethoxyphenyl) propane, 2,2-bis(4-(meth)acryloyloxytetraethoxyphenyl) propane, 2,2-bis(4-(meth)acryloyloxypentaethoxyphenyl) propane, 2,2-bis(4-(meth)acryloyloxydipropoxyphenyl) propane, 2-(4-(meth)acryloyloxydiethoxyphenyl)-2-(4-(meth)acryloyloxyethoxyphenyl)propane, 2-(4-(meth) acryloyloxydiethoxyphenyl)-2-(4-(meth) acryloyloxyditriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxypropoxyphenyl)propane, 2,2-bis(4-(meth) acryloyloxyisopropoxyphenyl)propane, 1,4-bis(2-(meth) acryloyloxyethyl) pyromellitate, and (meth)acrylamides of these compounds. These may be used alone or in combination with one another. Among the above examples, 2,2-bis (4-(meth)acryloyloxypolyethoxyphenyl)propane is preferred in that it has good miscibility with the (meth)acrylic acid ester polymer (a) and contributes to the good shape retention of a cure product of the dental polymerizable composition. Particularly preferred is 2,2-bis(4-(meth)acryloyloxypolyethoxyphenyl)propane in which the average number of moles of added ethoxy groups is 2.6 (commonly called "D2.6E").

Examples of the difunctional aliphatic (meth)acrylic acid esters and (meth)acrylamides include glycerol di(meth)acrylate, ethylene glycol di(meth)acrylate, diethylene glycol di(meth)acrylate, triethylene glycol di(meth)acrylate, propylene glycol di(meth)acrylate, butylene glycol di(meth) acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth) acrylate, 2-ethyl-1,6-hexanediol di(meth)acrylate, 1,9-nonanediol di(meth)acrylate, 1,10-decanediol di(meth)acrylate, 1,2-bis(3-methacryloyloxy-2-hydroxypropoxy)ethane, 2,2,4-trimethylhexamethylenebis(2-carbamoyloxyethyl) dimethacrylate (commonly called "UDMA"), and (meth) acrylamides of these compounds. Among these, glycerol di(meth)acrylate, triethylene glycol di(meth)acrylate, neopentyl glycol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, and 2,2,4-trimethylhexamethylenebis(2-carbamoyloxyethyl) dimethacrylate are preferred in that they have good miscibility with the (meth) acrylic acid ester polymer (a) and contribute to the good shape retention of a cured product of the resulting dental polymerizable composition. These may be used alone or in combination with one another.

Examples of the tri- or higher-functional (meth)acrylic acid esters and (meth)acrylamides include trimethylolpropane tri(meth)acrylate, trimethylolethane tri(meth)acrylate, trimethylolethane tri(meth)acrylate, pentaerythritol tri (meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol] tetramethacrylate, 1,7-diacryloyloxy-2,2,6,6-tetraacryloyloxymethyl-4-oxyheptane, and (meth) acrylamides of these compounds. Among these, trimethylolpropane tri(meth)acrylate is preferred in that it has good miscibility with the (meth)acrylic acid ester polymer (a).

One of the (meth)acrylic acid esters or the (meth)acrylamides mentioned above may be used alone as the polymerizable monomer (b). However, in terms of the curability of the dental polymerizable composition and the flexibility of its cured product, it is preferable to use a difunctional (meth)acrylic acid ester or (meth)acrylamide and a monofunctional (meth)acrylic acid ester or (meth)acrylamide in combination. The ratio between the difunctional (meth) acrylic acid ester or (meth)acrylamide and the monofunctional (meth)acrylic acid ester or (meth)acrylamide used in combination is not particularly limited. When the total amount of the polymerizable monomer (b) is defined as 100 weight %, the content of the difunctional (meth)acrylic acid ester or (meth)acrylamide is preferably 1 to 90 weight %, more preferably 2.5 to 80 weight %, and even more preferably 5 to 70 weight %. When the content of the difunctional (meth)acrylic acid ester or (meth)acrylamide is 70 weight % or less, a cured product of the dental polymerizable composition has high flexibility and is thus resistant to fracture. The total amount of the polymerizable monomer (b), as defined herein, refers to the total amount of the (meth)acrylic acid ester and (meth)acrylamide contained in the whole dental polymerizable composition. For example, when the dental polymerizable composition of the present invention is provided in a two-component form, the total amount of the polymerizable monomer (b) refers to the sum of the weight of a (meth)acrylic acid ester and/or (meth) acrylamide contained in one component and the weight of a (meth)acrylic acid ester and/or (meth)acrylamide contained in the other component.

The amount of the (meth)acrylic acid ester polymer (a) is preferably 5 to 500 parts by weight and more preferably 10 to 250 parts by weight per 100 parts by weight of the total amount of the (meth)acrylic acid ester and (meth)acrylamide as the polymerizable monomer (b).

Polymerization Initiator (c)

The polymerization initiator (c) used in the present invention can be selected for use from polymerization initiators used in general industrial fields and, in particular, polymerization initiators for dental use are preferably used. Specifically, a photopolymerization initiator (c-1) or a chemical polymerization initiator (c-2) can be used alone or two or more such initiators may be used in appropriate combination.

Examples of the photopolymerization initiator (c-1) include (bis)acylphosphine oxides, thioxanthones, quaternary ammonium salts of thioxanthones, ketals, α-diketones, coumarins, anthraquinones, benzoin alkyl ether compounds, and α-aminoketone compounds.

Among these examples of the photopolymerization initiator (c-1), at least one selected from the group consisting of (bis)acylphosphine oxides, salts thereof, and α-diketones is preferably used. In this case, the resulting dental polymerizable composition can have good photocurability under visible or near-ultraviolet light irradiation and show sufficient photocurability when irradiated using any light source selected from a halogen lamp, a light-emitting diode (LED), and a xenon lamp.

Examples of acylphosphine oxides among the (bis)acylphosphine oxides that may be used as the photopolymerization initiator (c-1) include 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, benzoyl di-(2,6-dimethylphenyl)phosphonate, 2,4,6-trimethylbenzoyldiphenylphosphine oxide sodium salt, 2,4,6-trimethylbenzoyldiphenylphosphine oxide potassium salt, and 2,4,6-trimethylbenzoyldiphenylphosphine oxide ammonium salt. Examples of bisacylphosphine oxides include bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis(2,5,6-trimethylbenzoyl)-2,4,4-trimethylpentylphosphine oxide. Additional examples include compounds as disclosed in JP 2000-159621 A.

Among these (bis)acylphosphine oxides, 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and 2,4,6-trimethylbenzoyldiphenylphosphine oxide sodium salt are particularly preferably used as the photopolymerization initiator (c-1).

Examples of the α-diketones that may be used as the photopolymerization initiator (c-1) include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferred in that it shows maximum absorption at a wavelength in the visible region.

Organic peroxides are preferably used as the chemical polymerization initiator (c-2) serving as the polymerization initiator (c). The organic peroxides that may be used as the chemical polymerization initiator (c-2) are not particularly limited, and commonly-known organic peroxides can be used. Typical examples of the organic peroxides include ketone peroxides, hydroperoxides, diacyl peroxides, dialkyl peroxides, peroxyketals, peroxyesters, and peroxydicarbonates.

Examples of the ketone peroxides that may be used as the chemical polymerization initiator (c-2) include methyl ethyl ketone peroxide, methyl isobutyl ketone peroxide, methyl cyclohexanone peroxide, and cyclohexanone peroxide.

Examples of the hydroperoxides that may be used as the chemical polymerization initiator (c-2) include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides that may be used as the chemical polymerization initiator (c-2) include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the dialkyl peroxides that may be used as the chemical polymerization initiator (c-2) include di-t-butyl peroxide, dicumyl peroxide, t-butyl cumyl peroxide, 2,5-dimethyl-2,5-di(t-butylperoxy)hexane, 1,3-bis(t-butylperoxyisopropyl)benzene, and 2,5-dimethyl-2,5-di(t-butylperoxy)-3-hexyne.

Examples of the peroxyketals that may be used as the chemical polymerization initiator (c-2) include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxyesters that may be used as the chemical polymerization initiator (c-2) include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, t-butyl peroxybenzoate, and t-butyl peroxyvaleric acid.

Examples of the peroxydicarbonates that may be used as the chemical polymerization initiator (c-2) include di-3-methoxy peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, the hydroperoxides are preferably used as the chemical polymerization initiator (c-2) in view of the overall balance of safety, storage stability, and radical formation potential in the presence of the (meth)acrylic acid ester polymer (a). Among the hydroperoxides, cumene hydroperoxide, t-butyl hydroperoxide, and 1,1,3,3-tetramethylbutyl hydroperoxide are particularly preferably used as the chemical polymerization initiator (c-2).

The content of the polymerization initiator (c) in the dental polymerizable composition of the present invention is not particularly limited. In terms of, for example, the curability of the resulting dental polymerizable composition, it is preferable that the polymerization initiator (c) be contained in an amount of 0.001 to 30 parts by weight per 100 parts by weight of the total amount of the (meth)acrylic acid ester and (meth)acrylamide as the polymerizable monomer (b). If the content of the polymerization initiator (c) is less than 0.001 parts by weight, the polymerization may fail to progress sufficiently, leading to undesired stickiness. The content of the polymerization initiator (c) is more preferably 0.05 parts by weight or more and even more preferably 0.1 parts by weight or more. If the content of the polymerization initiator (c) is more than 30 parts by weight when the polymerization initiator itself has low polymerizability, the initiator may be segregated from the dental polymerizable composition. The content of the polymerization initiator (c) is more preferably 20 parts by weight or less, even more preferably 15 parts by weight or less, and particularly preferably 10 parts by weight or less.

There is no other particular limitation on the dental polymerizable composition of the present invention, except that it should include the (meth)acrylic acid ester polymer (a), the polymerizable monomer (b), and the polymerization initiator (c) which have been described thus far. In an example, the dental polymerizable composition of the present invention may further include another component. The dental polymerizable composition of the present invention can be produced according to a commonly-known method.

Polymerization Accelerator (d)

It is preferable for the dental polymerizable composition of the present invention to include a polymerization accelerator (d). Examples of the polymerization accelerator (d) include amines, sulfinic acids, sulfinates, sulfites, hydrogen sulfites, aldehydes, thiourea compounds, organophosphorus compounds, borate compounds, barbituric acid derivatives, triazine compounds, vanadium compounds, copper compounds, tin compounds, halogen compounds, and thiol compounds.

The amines that may be used as the polymerization accelerator (d) are classified into aliphatic amines and aromatic amines. Examples of the aliphatic amines include: primary aliphatic amines such as n-butylamine, n-hexylamine, and n-octylamine; secondary aliphatic amines such as diisopropylamine, dibutylamine, and N-methylethanolamine; and tertiary aliphatic amines such as N-methyldiethanolamine, N-ethyldiethanolamine, N-n-butyldiethanolamine, N-lauryldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine.

Examples of the aromatic amines include N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-N,N-dimethylaminobenzoate, methyl 4-N,N-dimethylaminobenzoate, n-butoxyethyl N,N-dimethylaminobenzoate, 2-(methacryloyloxy)ethyl 4-N,N-dimethylaminobenzoate, 4-N,N-dimethylaminobenzophenone, and butyl 4-dimethylaminobenzoate. Among these, at least one selected from the group consisting of ethyl 4-N,N-dimethylaminobenzoate, n-butoxyethyl N,N-dimethylaminobenzoate, and 4-N,N-dimethylaminobenzophenone is preferably used, in terms of imparting good curability to the dental polymerizable composition.

Examples of the sulfinic acids and sulfinates that may be used as the polymerization accelerator (d) include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate.

Examples of the sulfites and hydrogen sulfites that may be used as the polymerization accelerator (d) include sodium sulfite, potassium sulfite, calcium sulfite, ammonium sulfite, sodium hydrogen sulfite, and potassium hydrogen sulfite.

Examples of the aldehydes that may be used as the polymerization accelerator (d) include terephthalaldehyde and benzaldehyde derivatives. Examples of the benzaldehyde derivatives include dimethylaminobenzaldehyde, p-methyloxybenzaldehyde, p-ethyloxybenzaldehyde, and p-n-octyloxybenzaldehyde.

Examples of the thiourea compounds that may be used as the polymerization accelerator (d) include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, 3,3-dimethylethylenethiourea, and 4,4-dimethyl-2-imidazolinethione. Among these, 1-(2-pyridyl)-2-thiourea or 4,4-dimethyl-2-imidazolinethione is preferably used as the polymerization accelerator (d) in terms of the curability of the dental polymerizable composition in the presence of the (meth)acrylic acid ester polymer (a).

Examples of the organophosphorus compounds that may be used as the polymerization accelerator (d) include triphenylphosphine, 2-methyltriphenylphosphine, 4-methyltriphenylphosphine, 2-methoxytriphenylphosphine, 4-methoxytriphenylphosphine, tri-n-butylphosphine, tri-isobutylphosphine, and tri-t-butylphosphine.

Tetravalent and/or pentavalent vanadium compounds are preferred as the vanadium compounds that may be used as the polymerization accelerator (d). Examples of the tetravalent and/or pentavalent vanadium compounds include vanadium(IV) oxide, vanadyl(IV) acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) oxide, sodium metavanadate(V), and ammonium metavanadate(V). Among these, vanadyl(IV) acetylacetonate is preferably used as the polymerization accelerator (d) in terms of the curability of the dental polymerizable composition in the presence of the (meth)acrylic acid ester polymer (a).

Examples of the copper compounds that may be used as the polymerization accelerator (d) include copper acetylacetonate, copper(II) acetate, copper oleate, copper(II) chloride, and copper(II) bromide. Among these, copper acetylacetonate or copper(II) acetate is preferably used as the polymerization accelerator (d) in terms of the curability of the dental polymerizable composition in the presence of the (meth)acrylic acid ester polymer (a).

Examples of the tin compounds that may be used as the polymerization accelerator (d) include di-n-butyltin dimaleate, di-n-octyltin dimaleate, di-n-octyltin dilaurate, and di-n-butyltin dilaurate. Among these, di-n-octyltin dilaurate or di-n-butyltin dilaurate is preferably used as the polymerization accelerator (d).

Examples of cobalt compounds that may be used as the polymerization accelerator (d) include cobalt acetylacetonate, cobalt acetate, cobalt oleate, cobalt chloride, and cobalt bromide.

Among these examples of the polymerization accelerator (d), the thiourea compounds, the vanadium compounds, and the copper compounds are particularly preferably used. Among these compounds, 1-(2-pyridyl)-2-thiourea, 4,4-dimethyl-2-imidazolinethione, vanadyl(IV) acetylacetonate, copper acetylacetonate, and copper(II) acetate are most preferably used as the polymerization accelerator (d).

The content of the polymerization accelerator (d) in the dental polymerizable composition is not particularly limited. In terms of, for example, the curability of the resulting dental polymerizable composition, it is preferable that the polymerization accelerator (d) be contained in an amount of 0.001 to 30 parts by weight per 100 parts by weight of the total amount of the (meth)acrylic acid ester and (meth)acrylamide as the polymerizable monomer (b). If the content of the polymerization accelerator (d) is less than 0.001 parts by weight, the polymerization may fail to progress sufficiently, leading to undesired stickiness. The content of the polymerization accelerator (d) is preferably 0.05 parts by weight or more and even more preferably 0.1 parts by weight or more. If the content of the polymerization accelerator (d) is more than 30 parts by weight when the polymerization initiator itself has low polymerizability, the polymerization initiator may be segregated from the dental polymerizable composition. The content of the polymerization accelerator (d) is preferably 20 parts by weight or less and more preferably 10 parts by weight or less.

The present invention may employ a combination of the chemical polymerization initiator (c-2) and the polymerization accelerator (d) to form a redox polymerization initiator system. In this case, the chemical polymerization initiator (c-2) and the polymerization accelerator (d) are stored in separate containers, respectively, in consideration of storage stability. The dental polymerizable composition is provided in a form that includes at least a first component containing the chemical polymerization initiator (c-2) and a second component containing the polymerization accelerator (d). It is preferable that the dental polymerizable composition be provided as a kit used in a two-component form composed of the first component and the second component. In this case, it is more preferable that the dental polymerizable composition be provided as a kit used in a two-paste form composed of the first and second components both of which are in a paste form. In such a case where the dental polymerizable composition is provided as a kit in a two-paste form, the two pastes are stored separately from each other and, immediately before use, the two pastes are kneaded together to allow chemical polymerization to take place. When the dental polymerizable composition further contains a photopolymerization initiator, it is preferable to allow not only chemical polymerization but also photopolymerization to take place to cure the dental polymerizable composition.

Filler (e)

The dental polymerizable composition of the present invention may further contain a filler (e) to adjust the paste properties or improve the mechanical strength of a cured product of the dental polymerizable composition. Examples of the filler (e) include an organic filler, an inorganic filler, and an organic-inorganic composite filler.

Examples of the material of the organic filler include polymethyl methacrylate, polyethyl methacrylate, methyl methacrylate-ethyl methacrylate copolymer, cross-linked polymethyl methacrylate, cross-linked polyethyl methacrylate, polyester, polyamide, polycarbonate, polyphenylene ether, polyoxymethylene, polyvinyl chloride, polystyrene, polyethylene, polypropylene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used alone or as a mixture of two or more thereof. The shape of the organic filler is not particularly limited, and the particle diameter of the filler can be selected as appropriate.

Examples of the material of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may also be used alone or as a mixture of two or more thereof. The shape of the inorganic filler is not particularly limited. An irregularly-shaped filler or a spherical filler can be selected for use as appropriate.

The above inorganic filler may optionally be surface-treated with a commonly-known surface treatment agent such as a silane coupling agent before use in order to adjust the miscibility with the polymerizable monomer (b). Examples of the surface treatment agent include vinyltrimethoxysilane, vinyltriethoxysilane, vinyltrichlorosilane, vinyl-tris($\beta$-methoxyethoxy)silane, 3-methacryloyloxypropyltrimethoxysilane, 11-methacryloyloxyundecyltrimethoxysilane, 3-glycidoxypropyltrimethoxysilane, 3-mercaptopropyltrimethoxysilane, and 3-aminopropyltriethoxysilane.

As for the technique for the surface treatment, commonly-known techniques can be used without particular limitation. Examples of the techniques include: a technique in which the above surface treatment agent is applied by spraying to the inorganic filler under vigorous stirring; a technique in which the inorganic filler and the above surface treatment agent are dispersed or dissolved in an appropriate solvent and then the solvent is removed; and a technique in which the alkoxy groups of the above surface treatment agent are hydrolyzed into silanol groups in an aqueous solution with the help of an acid catalyst so that the surface treatment agent is attached to the surface of the inorganic filler in the aqueous solution, and water is then removed. In any of these techniques, heating, usually at 50 to 150° C., can be used to fully complete the reaction between the surface of the inorganic filler and the surface treatment agent and thereby accomplish the surface treatment.

The organic-inorganic composite filler can be obtained, for example, by first adding a monomer to the above inorganic filler to form a paste, allowing the paste to undergo polymerization, and then crushing the resulting polymer. For example, a TMTP filler (filler obtained by mixing trimethylolpropane methacrylate and a silica filler, allowing the mixture to undergo polymerization, and then crushing the resulting polymer) can be used as the organic-inorganic composite filler. The shape of the organic-inorganic composite filler is not particularly limited, and the particle diameter of the filler can be selected as appropriate.

The average particle diameter of the filler (e) is preferably 0.001 to 100 μm and more preferably 0.001 to 50 μm in terms of, for example, the ease of handling of the resulting dental polymerizable composition and the mechanical strength of a cured product of the dental polymerizable composition. The average particle diameter of the filler (e)

as defined herein can be measured by any method known to persons skilled in the art and can be measured, for example, using a laser diffraction particle size distribution analyzer.

The content of the filler (e) is not particularly limited. In terms of the ease of handling of the resulting dental polymerizable composition and the mechanical strength of a cured product of the dental polymerizable composition, the content is preferably 500 parts by weight or less, more preferably 250 parts by weight or less, and even more preferably 100 parts by weight or less, per 100 parts by weight of the total amount of the (meth)acrylic acid ester polymer (a) and the (meth)acrylic acid ester and/or (meth)acrylamide as the polymerizable monomer (b). When the content of the filler (e) is 500 parts by weight or less, the good flexibility of a cured product of the dental polymerizable composition can be maintained.

Another polymer such as natural rubber, synthetic polyisoprene rubber, liquid polyisoprene rubber and a hydrogenated product thereof, polybutadiene rubber, liquid polybutadiene rubber and a hydrogenated product thereof, styrene-butadiene rubber, chloroprene rubber, ethylene-propylene rubber, acrylic rubber, isoprene-isobutylene rubber, acrylonitrile-butadiene rubber, or styrene elastomer, can be added to the dental polymerizable composition of the present invention for the purpose of modifying the properties such as flexibility and flowability as long as there is no departure from the gist of the present invention. Specific examples of the other polymer that can be added include polystyrene-polyisoprene-polystyrene block copolymer, polystyrene-polybutadiene-polystyrene block copolymer, poly(α-methylstyrene)-polybutadiene-poly(α-methylstyrene) block copolymer, poly(p-methylstyrene)-polybutadiene-poly(p-methylstyrene) block copolymer, and their hydrogenated products.

The dental polymerizable composition of the present invention may contain a softener where necessary. Examples of the softener include: petroleum-derived softeners such as paraffinic, naphthenic, and aromatic process oils; paraffin; and vegetable oil-derived softeners such as peanut oil and rosin. These softeners may be used alone or as a mixture of two or more thereof. The content of the softener is not particularly limited as long as there is no departure from the gist of the present invention. The content is typically 300 parts by weight or less and preferably 100 parts by weight or less per 100 parts by weight of the total amount of the (meth)acrylic acid ester polymer (a) and the (meth)acrylic acid ester and/or (meth)acrylamide as the polymerizable monomer (b).

Furthermore, the dental polymerizable composition of the present invention may contain a commonly-known additive to the extent that the additive causes no degradation in the performance of the composition. Examples of the additive include a polymerization inhibitor, an antioxidant, a pigment, a dye, an ultraviolet absorber, an organic solvent, and a thickener.

Examples of the polymerization inhibitor include hydroquinone, hydroquinone monomethyl ether, dibutylhydroquinone, dibutylhydroquinone monomethyl ether, t-butylcatechol, 2-t-butyl-4,6-dimethylphenol, 2,6-di-t-butylphenol, and 3,5-di-t-butyl-4-hydroxytoluene. The content of the polymerization inhibitor is preferably 0.001 to 1.0 parts by weight per 100 parts by weight of the total amount of the (meth)acrylic acid ester polymer (a) and the (meth)acrylic acid ester and/or (meth)acrylamide as the polymerizable monomer (b).

The dental polymerizable composition of the present invention shows good flexibility and shock-absorbing capacity after being cured. The dental polymerizable composition of the present invention can thus be used in applications to which such an advantage is beneficial. In particular, the composition is best suited for use in a denture liner and a dental tissue conditioner and is suitable also for use in a dental temporary cement and a dental filling material such as a root canal filling material or temporary sealing material.

An example of the preferred constitution of the denture liner, the dental tissue conditioner, the dental temporary cement, and the dental filling material is as follows. That is, it is preferable for the denture liner to include 5 to 250 parts by weight of the (meth)acrylic acid ester polymer (a), 0.05 to 15 parts by weight of the polymerization initiator (c), and 0.05 to 20 parts by weight of the polymerization accelerator (d) per 100 parts by weight of the total amount of the (meth)acrylic acid ester and/or (meth)acrylamide as the polymerizable monomer (b) and include 0 to 300 parts by weight of the filler (e) per 100 parts by weight of the total amount of the (meth)acrylic acid ester polymer (a) and the (meth)acrylic acid ester and/or (meth)acrylamide as the polymerizable monomer (b). It is more preferable for the denture liner to include 10 to 250 parts by weight of the (meth)acrylic acid ester polymer (a), 0.1 to 15 parts by weight of the polymerization initiator (c), and 0.1 to 10 parts by weight of the polymerization accelerator (d) per 100 parts by weight of the (meth)acrylic acid ester and/or (meth) acrylamide as the polymerizable monomer (b) and include 0 to 150 parts by weight of the filler (e) per 100 parts by weight of the total amount of the (meth)acrylic acid ester polymer (a) and the (meth)acrylic acid ester and/or (meth)acrylamide as the polymerizable monomer (b).

EXAMPLES

The present invention will now be described in detail with reference to examples. It should be noted that the present invention is not limited to the examples.

A (meth)acrylic acid ester polymer (a)-1, a (meth)acrylic acid ester polymer (a)-2, a (meth)acrylic acid ester polymer (a)-3, and a (meth)acrylic acid ester polymer (a)-4 were produced for use as the (meth)acrylic acid ester polymer (a) in dental polymerizable compositions of Examples. For use in dental polymerizable compositions of Comparative Examples, a (meth)acrylic acid ester block copolymer 1 (KURARITY L2250, manufactured by KURARAY CO., LTD., Mw: 78000) and a styrene block copolymer 1 (HYBRAR 5127, manufactured by KURARAY CO., LTD., Mw: 120000) were provided and, in addition, a (meth)acrylic acid ester polymer 1 and a (meth)acrylic acid ester polymer 2 were produced.

<GPC Measurement>

The weight-average molecular weight (Mw) and polydispersity (Mw/Mn (number average molecular weight)) of each of the produced (meth)acrylic acid ester polymer (a)-1, (meth)acrylic acid ester polymer (a)-2, (meth)acrylic acid ester polymer (a)-3, (meth)acrylic acid ester polymer (a)-4, (meth)acrylic acid ester polymer 1, and (meth)acrylic acid ester polymer 2 were determined by gel permeation chromatography on a polystyrene-equivalent basis. The GPC system used was a GPC system manufactured by Tosoh Corporation (HLC-8020). "TSKgel GMHXL", "G4000HXL", and "G5000HXL", which are manufactured by Tosoh Corporation, were connected in series in this order and used together as a separation column. Tetrahydrofuran was used as an eluent and fed to the separation column at a flow rate of 1.0 mL/min. The detection was conducted on the basis of ultraviolet absorptivity for the (meth)acrylic acid ester polymer (a)-4 and on the basis of differential refractive index for the above polymers other than the (meth)acrylic acid ester polymer (a)-4.

<Measurement of Tg and Tan δ at 37° C.>

Each of the produced (meth)acrylic acid ester polymer (a)-1, (meth)acrylic acid ester polymer (a)-2, (meth)acrylic acid ester polymer (a)-3, (meth)acrylic acid ester polymer (a)-4, (meth)acrylic acid ester polymer 1, and (meth)acrylic acid ester polymer 2 was subjected to dynamic mechanical analysis using a rheometer, "AR 2000" manufactured by TA Instruments Japan Inc., in an appropriate temperature range, and Tg and tan δ at 37° C. of each polymer were determined. In this dynamic mechanical analysis, the shear rate was set to 100 Hz. A temperature at which tan δ reaches a peak was determined as the glass transition temperature Tg.

<Melting Point Measurement>

Each of the produced (meth)acrylic acid ester polymer (a)-1, (meth)acrylic acid ester polymer (a)-2, (meth)acrylic acid ester polymer (a)-3, (meth)acrylic acid ester polymer (a)-4, (meth)acrylic acid ester polymer 1, and (meth)acrylic acid ester polymer 2 was subjected to melting point measurement using a differential scanning calorimeter (DSC), "Q2000" manufactured by TA Instruments Japan Inc., in an appropriate temperature range. The temperature rise rate was set to 10° C./min. No endothermic peak was observed for all of the polymers, which confirmed that none of the polymers had a melting point.

<(Meth)Acrylic Acid Ester Polymer (a)-1>

The (meth)acrylic acid ester polymer (a)-1 was produced as follows. A three-way cock was attached to a 1 liter three-neck flask, the interior of which was degassed and purged with nitrogen and into which 390 g of toluene, 1.4 ml of N,N',N',N'',N''-pentamethyldiethylenetriamine, and 18 ml of a toluene solution containing 11 mmol of isobutylbis(2,6-di-t-butyl-4-methylphenoxy)aluminum were then added at room temperature, followed by 1.7 ml of a cyclohexane/n-hexane mixture solution containing 2.2 mmol of sec-butyllithium. To the resulting solution was added 150 ml of neopentyl methacrylate, and the solution was stirred at room temperature for 10 hours. Methanol in an amount of 1 g was added to the reaction solution to terminate the polymerization. After the termination of polymerization, the reaction solution was poured into a large amount of liquid mixture of methanol and water (methanol: 90 weight %), and the resulting white precipitate produced was collected to obtain the (meth)acrylic acid ester polymer (a)-1.

Mw, Mw/Mn, Tg, and tan δ at 37° C. were measured for the thus-produced (meth)acrylic acid ester polymer (a)-1 using the above methods. Mw was 75,000, Mw/Mn was 1.15, Tg was 36.2° C., and tan δ at 37° C. was 0.72.

<(Meth)Acrylic Acid Ester Polymer (a)-2>

The (meth)acrylic acid ester polymer (a)-2 was produced as follows. A three-way cock was attached to a 1 liter three-neck flask, the interior of which was degassed and purged with nitrogen and into which 390 g of toluene, 1.0 ml of N,N',N',N'',N''-pentamethyldiethylenetriamine, and 12 ml of a toluene solution containing 11 mmol of isobutylbis(2,6-di-t-butyl-4-methylphenoxy)aluminum were then added at room temperature, followed by 1.3 ml of a cyclohexane/n-hexane mixture solution containing 2.2 mmol of sec-butyllithium. To the resulting solution was added 150 ml of a liquid mixture of 12 weight % of methyl methacrylate and 88 weight % of n-butyl methacrylate, and the solution was stirred at room temperature for 10 hours. Methanol in an amount of 1 g was added to the reaction solution to terminate the polymerization. After the termination of polymerization, the reaction solution was poured into a large amount of liquid mixture of methanol and water (methanol: 90 weight %), and the resulting white precipitate produced was collected to obtain the (meth)acrylic acid ester polymer (a)-2.

Mw, Mw/Mn, Tg, and tan δ at 37° C. were measured for the thus-produced (meth)acrylic acid ester polymer (a)-2 using the above methods. Mw was 120,000, Mw/Mn was 1.18, Tg was 37.5° C., and tan δ at 37° C. was 0.57.

<(Meth)Acrylic Acid Ester Polymer (a)-3>

The (meth)acrylic acid ester polymer (a)-3 was produced as follows. A three-way cock was attached to a 1 liter three-neck flask, the interior of which was degassed and purged with nitrogen and into which 390 g of toluene, 1.4 ml of N,N',N',N'',N''-pentamethyldiethylenetriamine, and 10 ml of a toluene solution containing 11 mmol of isobutylbis(2,6-di-t-butyl-4-methylphenoxy)aluminum were then added at room temperature, followed by 1.0 ml of a cyclohexane/n-hexane mixture solution containing 2.2 mmol of sec-butyllithium. To the resulting solution was added 150 ml of a liquid mixture of 33 weight % of isobutyl methacrylate and 67 weight % of n-butyl methacrylate, and the solution was stirred at room temperature for 10 hours. Methanol in an amount of 1 g was added to the reaction solution to terminate the polymerization. After the termination of polymerization, the reaction solution was poured into a large amount of liquid mixture of methanol and water (methanol: 90 weight %), and the resulting white precipitate produced was collected to obtain the (meth)acrylic acid ester polymer (a)-3.

Mw, Mw/Mn, Tg, and tan δ at 37° C. were measured for the thus-produced (meth)acrylic acid ester polymer (a)-3 using the above methods. Mw was 180,000, Mw/Mn was 1.2, Tg was 35.8° C., and tan δ at 37° C. was 0.68.

<(Meth)Acrylic Acid Ester Polymer (a)-4>

The (meth)acrylic acid ester polymer (a)-4 was produced as follows. A three-way cock was attached to a 1 liter three-neck flask, the interior of which was degassed and purged with nitrogen and into which 390 g of toluene, 0.8 ml of N,N',N',N'',N''-pentamethyldiethylenetriamine, and 8 ml of a toluene solution containing 11 mmol of isobutylbis(2,6-di-t-butyl-4-methylphenoxy)aluminum were then added at room temperature, followed by 0.8 ml of a cyclohexane/n-hexane mixture solution containing 2.2 mmol of sec-butyllithium. To the resulting solution was added 150 ml of a liquid mixture of 70 weight % of isobutyl methacrylate and 30 weight % of 2-ethylhexyl methacrylate, and the solution was stirred at room temperature for 10 hours. Methanol in an amount of 1 g was added to the reaction solution to terminate the polymerization. After the termination of polymerization, the reaction solution was poured into a large amount of liquid mixture of methanol and water (methanol: 90 weight %), and the resulting white precipitate produced was collected to obtain the (meth)acrylic acid ester polymer (a)-4.

Mw, Mw/Mn, Tg, and tan δ at 37° C. were measured for the thus-produced (meth)acrylic acid ester polymer (a)-4 using the above methods. Mw was 250,000, Mw/Mn was 1.21, Tg was 35.6° C., and tan δ at 37° C. was 0.59.

<(Meth)Acrylic Acid Ester Polymer 1>

The (meth)acrylic acid ester polymer 1 was produced as follows. A three-way cock was attached to a 1 liter three-neck flask, the interior of which was degassed and purged with nitrogen and into which 390 g of toluene, 1.4 ml of N,N',N',N'',N''-pentamethyldiethylenetriamine, and 18 ml of a toluene solution containing 11 mmol of isobutylbis(2,6-di-t-butyl-4-methylphenoxy)aluminum were then added at room temperature, followed by 1.7 ml of a cyclohexane/n-hexane mixture solution containing 2.2 mmol of sec-butyllithium. To the resulting solution was added 150 ml of methyl methacrylate, and the solution was stirred at room temperature for 10 hours. Methanol in an amount of 1 g was added to the reaction solution to terminate the polymerization. After the termination of polymerization, the reaction solution was poured into a large amount of liquid mixture of methanol and water (methanol: 90 weight %), and the resulting white precipitate produced was collected to obtain the (meth)acrylic acid ester polymer 1.

Mw, Mw/Mn, Tg, and tan δ at 37° C. were measured for the thus-produced (meth)acrylic acid ester polymer 1 using the above methods. Mw was 74,000, Mw/Mn was 1.13, Tg was 103° C., and tan δ at 37° C. was 0.09.

<(Meth)Acrylic Acid Ester Polymer 2>

The (meth)acrylic acid ester polymer 2 was produced as follows. A three-way cock was attached to a 1 liter three-neck flask, the interior of which was degassed and purged with nitrogen and into which 390 g of toluene, 1.4 ml of N,N',N',N'',N''-pentamethyldiethylenetriamine, and 18 ml of a toluene solution containing 11 mmol of isobutylbis(2,6-di-t-butyl-4-methylphenoxy)aluminum were then added at room temperature, followed by 1.7 ml of a cyclohexane/n-hexane mixture solution containing 2.2 mmol of sec-butyl-lithium. To the resulting solution was added 150 ml of 2-ethylhexyl methacrylate, and the solution was stirred at room temperature for 10 hours. Methanol in an amount of 1 g was added to the reaction solution to terminate the polymerization. After the termination of polymerization, the reaction solution was poured into a large amount of liquid mixture of methanol and water (methanol: 90 weight %), and the resulting white precipitate produced was collected to obtain the (meth)acrylic acid ester polymer 2.

Mw, Mw/Mn, Tg, and tan δ at 37° C. were measured for the thus-produced (meth)acrylic acid ester polymer 2 using the above methods. Mw was 79,000, Mw/Mn was 1.16, Tg was −11° C., and tan δ at 37° C. was 0.07.

The following lists the components used in polymerizable compositions according to Examples or Comparative Examples along with their abbreviations.

[Polymerizable Monomer (b)]
3G: Triethylene glycol dimethacrylate
D-2.6E: 2,2-bis(4-methacryloyloxypolyethoxyphenyl)propane
UDMA: 2,2,4-trimethylhexamethylenebis(2-carbamoyloxyethyl) dimethacrylate
DFHM: 1H,1H,7H-dodecafluoroheptyl methacrylate
BEM: Butoxyethyl methacrylate
[Photopolymerization Initiator (c-1)]
CQ: Camphorquinone
BAPO: Bis(2,4,6-trimethylbenzoyl)phenylphosphine oxide
[Chemical polymerization initiator (c-2)]
THP: 1,1,3,3-tetramethylbutyl hydroperoxide
CHP: Cumene hydroperoxide
[Polymerization Accelerator (d)]
PDE: Ethyl N,N-dimethylaminobenzoate
PTU: 1-(2-pyridyl)-2-thiourea
DMETU: 4,4-dimethyl-2-imidazolinethione
VOAA: Vanadyl(IV) acetylacetonate
CUA: Copper(II) acetate
[Filler (e)]
Filler (e)-1: Colloidal silica powder ("Aerosil OX50" manufactured by Nippon Aerosil Co., Ltd.)
Filler (e)-2: Colloidal silica powder ("Aerosil 380" manufactured by Nippon Aerosil Co., Ltd.)
[Polymerization Inhibitor]
BHT: 3,5-di-t-butyl-4-hydroxytoluene The components were mixed in proportions shown in Table 1 at ordinary temperature (20° C.±15° C., specified in Japanese Industrial Standards (JIS) Z 8703) to prepare pastes A and pastes B as dental polymerizable compositions according to Examples 1 to 7. In each example, the paste A and the paste B were kneaded together, and a kneaded mixture of the paste A and the paste B was irradiated with light using a light irradiator. In this way, cured products according to Examples 1 to 7 were obtained.

The components were mixed in proportions shown in Table 2 at ordinary temperature to prepare pastes A and pastes B as dental polymerizable compositions according to Comparative Examples 1 to 4. In Comparative Example 2, the styrene block copolymer was insoluble in the polymerizable monomer (b). In Comparative Example 1, Comparative Example 3, and Comparative Example 4, the paste A and the paste B were kneaded together, and a kneaded mixture of the paste A and the paste B was irradiated with light using a light irradiator. In this way, cured products according to Comparative Example 1, Comparative Example 3, and Comparative Example 4 were obtained.

<Flexibility Test>

A disc-shaped test specimen of 1.5 cm diameter×0.2 cm thickness was prepared for each of the cured products according to Examples and Comparative Examples. The test specimen was used to measure the hardness (A hardness) of the cured product at 37° C. with a type A durometer according to JIS K 7215, and the hardness was adopted as a measure of the flexibility. The results are shown in Table 1 and Table 2. A cured product that shows an A hardness of 50 or less at 37° C. in this measurement can be considered superior in flexibility.

<Shock-Absorbing Capacity (Tan δ)>

Each of the cured products according to Examples and Comparative Examples was set on a rheometer (manufactured by TA Instruments Japan Inc., trade name: AR 2000) and rotated in one direction at temperatures ranging from 0 to 60° C. at a shear rate of 100 Hz using a 20-mm-diameter parallel plate to measure tan δ. The results are shown in Table 1 and Table 2. A cured product that shows tan δ at 37° C. of 0.10 or more in this measurement can be considered superior in shock-absorbing capacity.

<Shape Retention (Compression Set)>

A disc-shaped test specimen of 1.5 cm diameter×0.5 cm thickness was prepared for each of the cured products according to Examples and Comparative Examples. The test specimen was used to measure the compression set caused by exposure to conditions of a temperature of 37° C. and a compression deformation of 25% for 24 hours. The compression set was calculated by the formula below. The results are shown in Table 1 and Table 2. A cured product that shows a compression set at 37° C. of 30% or less in this measurement can be considered superior in shape retention.

Compression set [%]={0.5−(thickness measured after test)}/0.1×100

<Transparency Test>

Each of the dental polymerizable compositions (pastes A and pastes B) according to Examples and Comparative Examples was kneaded and charged into a mold made of SUS (having dimensions of 2 mm×20 mm Dia.). Glass slides were then pressed against the upper and lower surfaces of the dental polymerizable composition charged in the mold. Next, six points of each of the two surfaces of the dental polymerizable composition charged in the mold were irradiated with light for 10 seconds each using a dental visible light irradiation device (Pencure 2000 manufactured by Morita Corporation) to cure the dental polymerizable composition. The transparency ΔL of the resulting cured product was measured using a spectrophotometric colorimeter (manufactured by NIPPON DENSHOKU INDUSTRIES CO., LTD., SE 2000, illuminant D65). The transparency ΔL is defined by the formula below. To achieve a high aesthetic quality, the transparency (ΔL) needs to be 50 or more. The results are shown in Table 1 and Table 2.

$$\Delta L = L^*W - L^*B$$

L*W represents a lightness index L* in L*a*b color system as measured against a white background, while L*B represents a lightness index L* in L*a*b color system as measured against a black background.

<Stain Resistance Test>

Each cured product obtained in the same manner as in the transparency test was subjected to colorimetry using a spectrophotometric colorimeter (manufactured by NIPPON DENSHOKU INDUSTRIES CO., LTD., SE 2000, illuminant D65), and the measured chromaticity was defined as a pre-staining chromaticity. Next, the cured product was immersed in a coffee containing 1 weight % of dispersed coffee grains at 37° C. for 1 day, after which the colorimetry was conducted again. The thus-measured chromaticity was defined as a post-staining chromaticity. The difference between the pre-staining chromaticity and the post-staining chromaticity was evaluated as ΔE. ΔE is defined by the formula below. To achieve good color stability of the cured product of the dental polymerizable composition, ΔE needs to be 3 or less. The results are shown in Table 1 and Table 2.

$$\Delta E = \{(L^*1 - L^*2)^2 + (a^*1 - a^*2)^2 + (b^*1 - b^*2)^2\}^{1/2}$$

L*1, a*1, b*1, L*2, a*2, and b*2 are indices representing chromaticities (L*, a*, b*) in L*a*b* color system measured with the spectrophotometric colorimeter. The chromaticity (L*1, a*1, b*1) represents the post-staining chromaticity, while the chromaticity (L*2, a*2, b*2) represents the pre-staining chromaticity.

As shown in Table 1 and Table 2, the cured products of the dental polymerizable compositions according to Examples 1 to 7 were superior in flexibility, shock-absorbing capacity, shape retention, transparency, and stain resistance. In particular, the flexibility of the cured products of the dental polymerizable compositions according to Examples 1 to 7 was better than that of the cured products of the dental polymerizable compositions according to Comparative Example 1 and Comparative Example 3. The shock-absorbing capacity of the dental polymerizable compositions according to Examples 1 to 7 was higher than the shock-absorbing capacity of the cured products of the dental polymerizable compositions according to Comparative Example 1, Comparative Example 3, and Comparative Example 4. The shape retention of the cured products of the dental polymerizable compositions according to Examples 1 to 7 was better than the shape retention of the cured products of the dental polymerizable compositions according to Comparative Example 3 and Comparative Example 4. The stain resistance of the cured products of the dental polymerizable compositions according to Examples 1 to 7 was higher than the stain resistance of the cured product of the dental polymerizable composition according to Comparative Example 4.

TABLE 1

| | | Example 1 | | Example 2 | | Example 3 | | Example 4 | | Example 5 | | Example 6 | | Example 7 | |
|---|---|---|---|---|---|---|---|---|---|---|---|---|---|---|---|
| | | A | B | A | B | A | B | A | B | A | B | A | B | A | B |
| (Meth)acrylic acid ester polymer (a)-1 [parts by weight] | | 250 | 250 | | | | | | | | | 50 | 50 | | |
| (Meth)acrylic acid ester polymer (a)-2 [parts by weight] | | | | 150 | 150 | | | | | | | | | | |
| (Meth)acrylic acid ester polymer (a)-3 [parts by weight] | | | | | | 100 | 100 | | | 100 | 100 | 50 | 50 | 100 | 100 |
| (Meth)acrylic acid ester polymer (a)-4 [parts by weight] | | | | | | | | 50 | 50 | | | | | | |
| Polymerizable monomer (b) | 3G [parts by weight] | 5 | 5 | 5 | 5 | 5 | 5 | 5 | 5 | 10 | 10 | 5 | 5 | | |
| | D-2.6E [parts by weight] | | | | | | | | | 10 | 10 | | | | |
| | UDMA [parts by weight] | 5 | 5 | 5 | 5 | 5 | 5 | 5 | 5 | | | 5 | 5 | 40 | 20 |
| | DFHM [parts by weight] | 90 | 90 | 90 | 90 | 90 | 90 | 90 | 90 | 40 | 40 | 90 | 90 | 60 | 80 |
| | BEM [parts by weight] | | | | | | | | | 40 | 40 | | | | |
| Photopolymerization initiator (c-1) | CQ [parts by weight] | 0.4 | | 0.4 | | 0.3 | | 0.3 | | 0.3 | | 0.3 | | 0.3 | |
| | BAPO [parts by weight] | 0.1 | | 0.05 | | 0.05 | | 0.05 | | 0.05 | | 0.05 | | 0.05 | |
| Chemical polymerization initiator (c-2) | THP [parts by weight] | | 3.0 | | 2.5 | | 1.5 | | 1.5 | | | | 1.5 | | 1.5 |
| | CHP [parts by weight] | | | | | | | | | | 1.5 | | | | |
| Polymerization accelerator (d) | PDE [parts by weight] | | 0.6 | | 0.6 | | 0.45 | | 0.45 | | 0.45 | | 0.45 | | 0.45 |
| | PTU [parts by weight] | | 3.0 | | 2.5 | | 1.5 | | 1.5 | | | | 1.5 | | 1.5 |
| | DMETU [parts by weight] | | | | | | | | | | 3.0 | | | | |
| | VOAA [parts by weight] | | 0.15 | | 0.1 | | 0.1 | | 0.1 | | | | 0.1 | | 0.1 |
| | CUA [parts by weight] | | | | | | | | | | 0.01 | | | | |

TABLE 1-continued

|  |  | Example 1 | | Example 2 | | Example 3 | | Example 4 | | Example 5 | | Example 6 | | Example 7 | |
|---|---|---|---|---|---|---|---|---|---|---|---|---|---|---|---|
|  |  | A | B | A | B | A | B | A | B | A | B | A | B | A | B |
| Filler (e) | Filler (e)-1 [parts by weight] | 50 | 50 | 25 | 25 |  |  |  |  |  |  |  |  |  |  |
|  | Filler (e)-2 [parts by weight] | 5.0 | 5.0 | 5.0 | 5.0 | 5.0 | 5.0 |  |  | 5.0 | 5.0 | 5.0 | 5.0 | 5.0 | 5.0 |
| Polymerization inhibitor | BHT [parts by weight] | 0.05 | 0.05 | 0.05 | 0.05 | 0.05 | 0.05 | 0.05 | 0.05 | 0.05 | 0.05 | 0.05 | 0.05 | 0.05 | 0.05 |
| Flexibility (A hardness) |  | 26 | | 28 | | 30 | | 35 | | 34 | | 32 | | 28 | |
| Shock-absorbing capacity (tan δ) |  | 0.32 | | 0.21 | | 0.26 | | 0.18 | | 0.22 | | 0.21 | | 0.22 | |
| Shape retention (compression set) [%] |  | 27 | 26 | 23 | 28 | 25 | 24 | 24 | | | | | | | |
| Transparency (ΔL) |  | 64 | 78 | 85 | 88 | 83 | 79 | 80 | | | | | | | |
| Stain resistance (ΔE) |  | 2.3 | 2.1 | 1.6 | 1.5 | 2.8 | 2.3 | 2.4 | | | | | | | |

TABLE 2

|  |  | Comparative Example 1 | | Comparative Example 2 | | Comparative Example 3 | | Comparative Example 4 | |
|---|---|---|---|---|---|---|---|---|---|
|  |  | A | B | A | B | A | B | A | B |
| (Meth)acrylic acid ester block copolymer 1 [parts by weight] |  | 100 | 100 |  |  |  |  |  |  |
| Styrene block copolymer 1 [parts by weight] |  |  |  | 100 | 100 |  |  |  |  |
| (Meth)acrylic acid ester polymer 1 [parts by weight] |  |  |  |  |  | 100 | 100 |  |  |
| (Meth)acrylic acid ester polymer 2 [parts by weight] |  |  |  |  |  |  |  | 100 | 100 |
| Polymerizable monomer (b) | 3G [parts by weight] | 5 | 5 | 5 | 5 | 5 | 5 | 5 | 5 |
|  | UDMA [parts by weight] | 5 | 5 | 5 | 5 | 5 | 5 | 5 | 5 |
|  | DFHM [parts by weight] | 90 | 90 | 90 | 90 | 90 | 90 | 90 | 90 |
| Photopolymerization initiator (c-1) | CQ [parts by weight] | 0.3 | | 0.3 | | 0.3 | | 0.3 | |
|  | BAPO [parts by weight] | 0.05 | | 0.05 | | 0.05 | | 0.05 | |
| Chemical polymerization initiator (c-2) | THP [parts by weight] | | 1.5 | | 1.5 | | 1.5 | | 1.5 |
| Polymerization accelerator (d) | PDE [parts by weight] | | 0.45 | | 0.45 | | 0.45 | | 0.45 |
|  | PTU [parts by weight] | | 1.5 | | 1.5 | | 1.5 | | 1.5 |
|  | VOAA [parts by weight] | | 0.1 | | 0.1 | | 0.1 | | 0.1 |
| Filler (e) | Filler (e)-2 [parts by weight] | 5.0 | 5.0 | 5.0 | 5.0 | 5.0 | 5.0 | 5.0 | 5.0 |
| Polymerization inhibitor | BHT [parts by weight] | 0.05 | 0.05 | 0.05 | 0.05 | 0.05 | 0.05 | 0.05 | 0.05 |
| Flexibility (A hardness) |  | 58 | | — | | 85 | | 99 | |
| Shock-absorbing capacity (tan δ) |  | 0.08 | | — | | 0.03 | | 0.05 | |
| Shape retention(compression set) [%] |  | 28 | | — | | 45 | | 52 | |
| Transparency (ΔL) |  | 84 | | — | | 82 | | 78 | |
| Stain resistance (ΔE) |  | 2.3 | | — | | 2.1 | | 10.4 | |

INDUSTRIAL APPLICABILITY

The dental polymerizable composition of the present invention shows good flexibility and shock-absorbing capacity when cured and is thus particularly suitable for use in denture liners and dental tissue conditioners. The dental polymerizable composition is suitable also for use in dental temporary cements and dental filling materials such as root canal filling materials and temporary sealing materials.

The invention claimed is:

1. A dental polymerizable composition, comprising:
   (a) a (meth)acrylic acid ester polymer (a) comprising a (meth)acrylic acid ester homopolymer (1) having a glass transition temperature of 25° C. to 50° C., and/or a random copolymer (2) of a (meth)acrylic acid ester (i) and a (meth)acrylic acid ester (ii);
   wherein
   a glass transition temperature of a homopolymer of the (meth)acrylic acid ester (i) is higher than 37° C.,
   a glass transition temperature of a homopolymer of the (meth)acrylic acid ester (ii) is lower than 37° C.,
   a glass transition temperature of the (meth)acrylic acid ester polymer (a) is from 25° C. to 50° C.,
   a tan δ at 37° C. of the (meth)acrylic acid ester polymer (a) is 0.10 or more as determined by dynamic mechanical analysis, and
   the (meth)acrylic acid ester polymer (a) has no melting point;
   (b) a polymerizable monomer (b) comprising a (meth)acrylic acid ester, a (meth)acrylamide, or both; and
   (c) a polymerization initiator (c).

2. The dental polymerizable composition according to claim 1, wherein the (meth)acrylic acid ester polymer (a) is dissolved in the polymerizable monomer (b).

3. The dental polymerizable composition according to claim 1, further comprising:
   (d) a polymerization accelerator (d).

4. The dental polymerizable composition according to claim 2, further comprising:

(d) a polymerization accelerator (d).

5. A dental temporary cement, comprising the dental polymerizable composition according to claim 1.

6. A dental filling material, comprising the dental polymerizable composition according to claim 1.

7. A denture liner, comprising the dental polymerizable composition according to claim 1.

8. A dental tissue conditioner, comprising the dental polymerizable composition according to claim 1.

* * * * *